United States Patent
Torii

(10) Patent No.: US 6,482,149 B1
(45) Date of Patent: Nov. 19, 2002

(54) CURVED PART OF ENDOSCOPE

(75) Inventor: Yuichi Torii, Omiya (JP)

(73) Assignee: Fuji Photo Optical Co., Ltd., Omiya (JP)

(*) Notice: Subject to any disclaimer, the term of this patent is extended or adjusted under 35 U.S.C. 154(b) by 0 days.

(21) Appl. No.: 09/568,697

(22) Filed: May 11, 2000

(30) Foreign Application Priority Data

| May 12, 1999 | (JP) | ............................................ 11-131292 |
| Jun. 1, 1999 | (JP) | ............................................ 11-153555 |
| Sep. 16, 1999 | (JP) | ............................................ 11-262544 |
| Apr. 20, 2000 | (JP) | ...................................... 2000-119252 |

(51) Int. Cl.[7] ................................................ A61B 1/00
(52) U.S. Cl. ........................ 600/142; 600/146; 600/141
(58) Field of Search ................................ 600/139, 141, 600/144, 146, 149, 142

(56) References Cited

U.S. PATENT DOCUMENTS

| 3,190,286 A | * | 6/1965 | Stokes ........................ 600/146 |
| 4,432,349 A | * | 2/1984 | Oshiro ........................ 600/149 |
| 4,700,693 A | * | 10/1987 | Lia et al. ..................... 600/141 |
| 4,796,607 A | * | 1/1989 | Allred et al. ................ 600/141 |
| 4,834,069 A | * | 5/1989 | Umeda ........................ 600/149 |
| 5,749,828 A | * | 5/1998 | Solomon et al. ............ 600/139 |

FOREIGN PATENT DOCUMENTS

| JP | A 62-292134 | 12/1987 |
| JP | 3-68326 | 3/1991 |
| JP | Y2 7-37601 | 8/1995 |
| JP | 9-294710 | 11/1997 |

\* cited by examiner

*Primary Examiner*—Linda C. M. Dvorak
*Assistant Examiner*—Jocelyn Ram
(74) *Attorney, Agent, or Firm*—Oliff & Berridge, PLC

(57) ABSTRACT

A curve control wire, which is inserted in a curved part of an endoscope, is inserted and guided in guide holes of connecting pins, which are rotatably provided inside a plurality of joint rings. A body of the connecting pin is inserted into a hole formed in the joint ring, and the connecting pin body is provided with a flange for preventing the body from falling into the inside of the joint ring and an annular plate for preventing the body from falling to the outside of the joint ring. By such a structure, the curve control wire can be easily inserted into the guide holes. A protection member is attached to the end of the connecting pin. The outer peripheral face of the protection member is made of a material softer than internal members, which are arranged inside the curved part, such as a light guide, a signal cable, a forceps tube, and an air and water supply tube. Thus, the internal members are prevented from being damaged. The joint rings are connected such that intervals between the bodies of the joint rings become gradually larger from the manual control part side of the curved part to the tip component side of the curved part. Thereby, a view area from an objective optical system arranged in the tip component becomes large.

5 Claims, 17 Drawing Sheets

F I G. 4
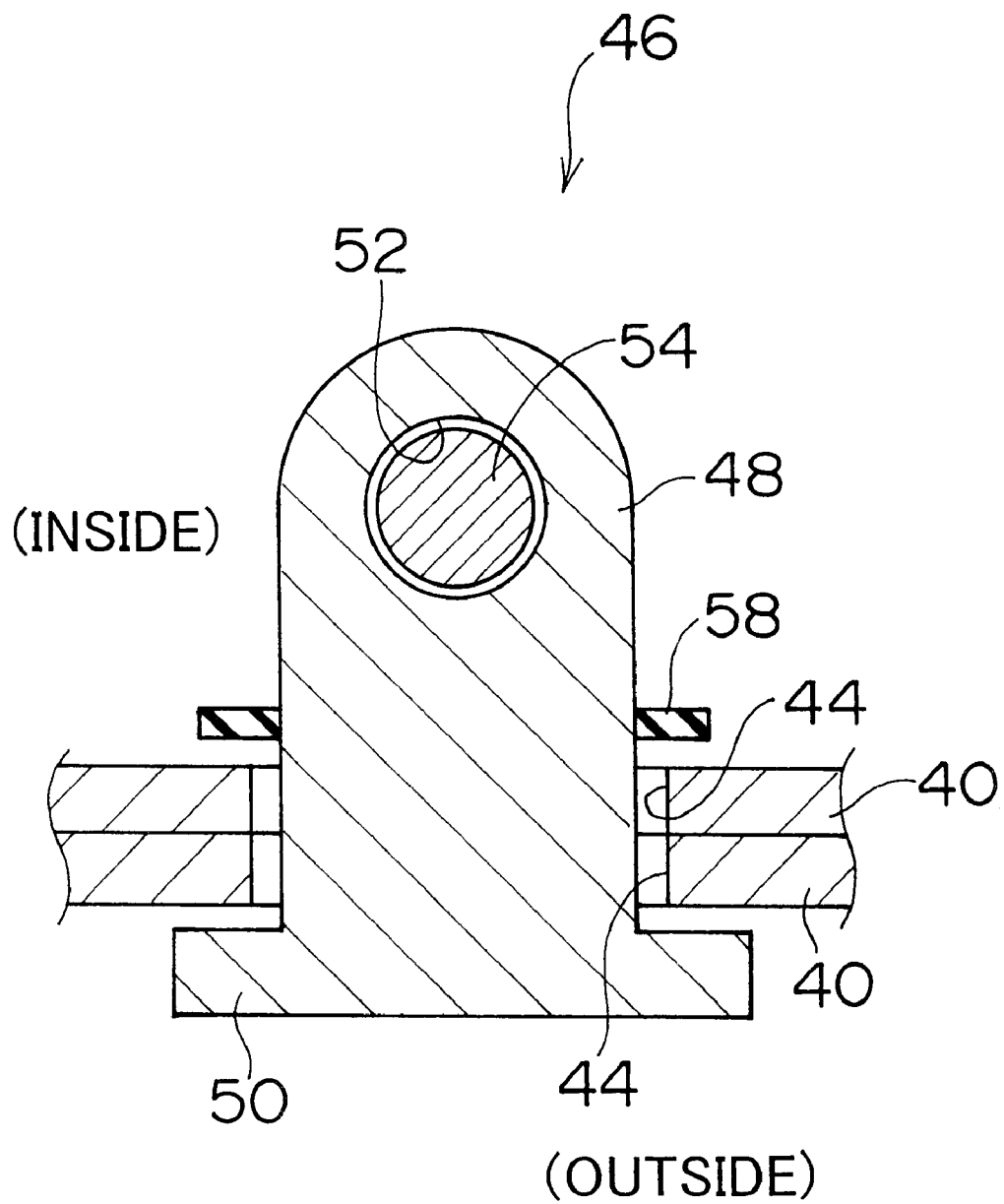

F I G. 7
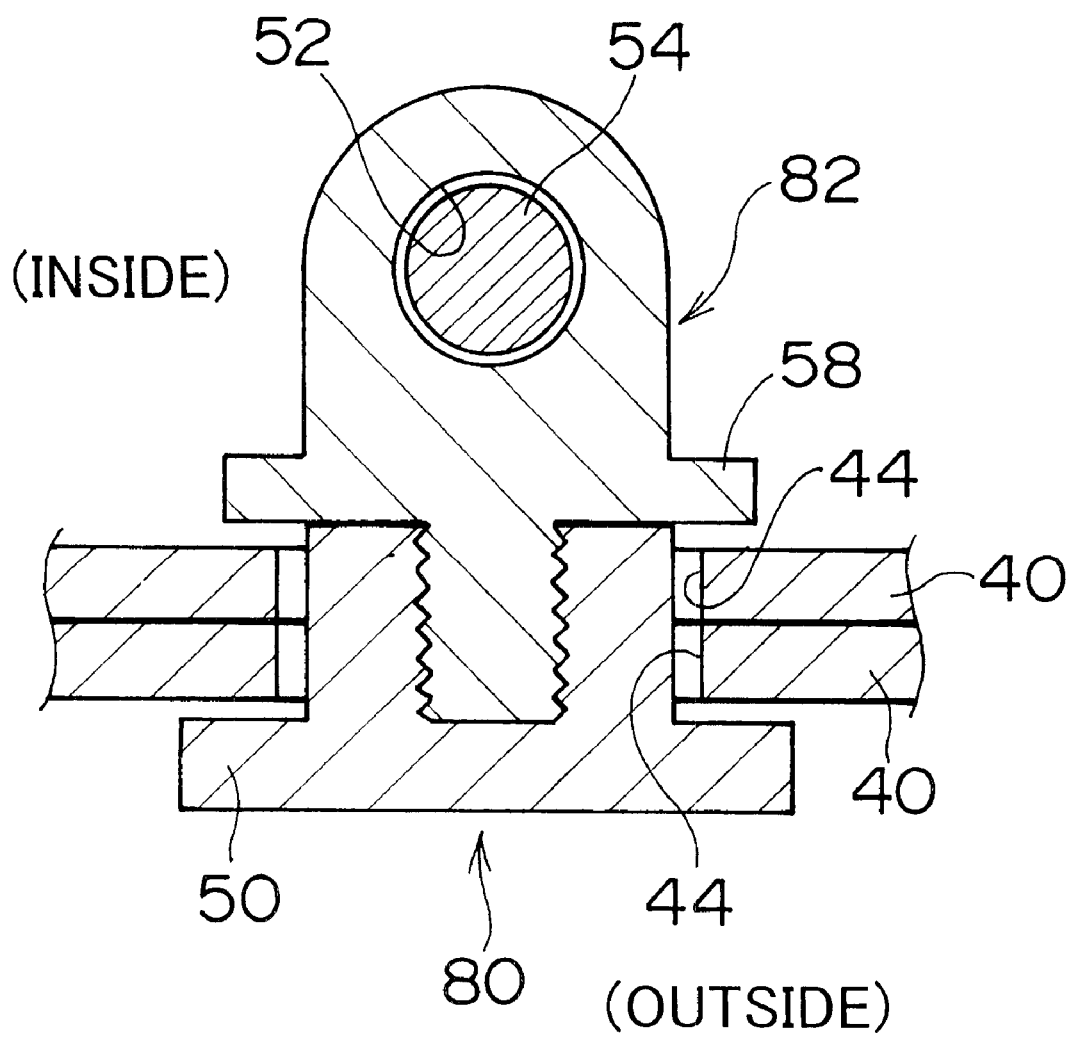

F I G. 9
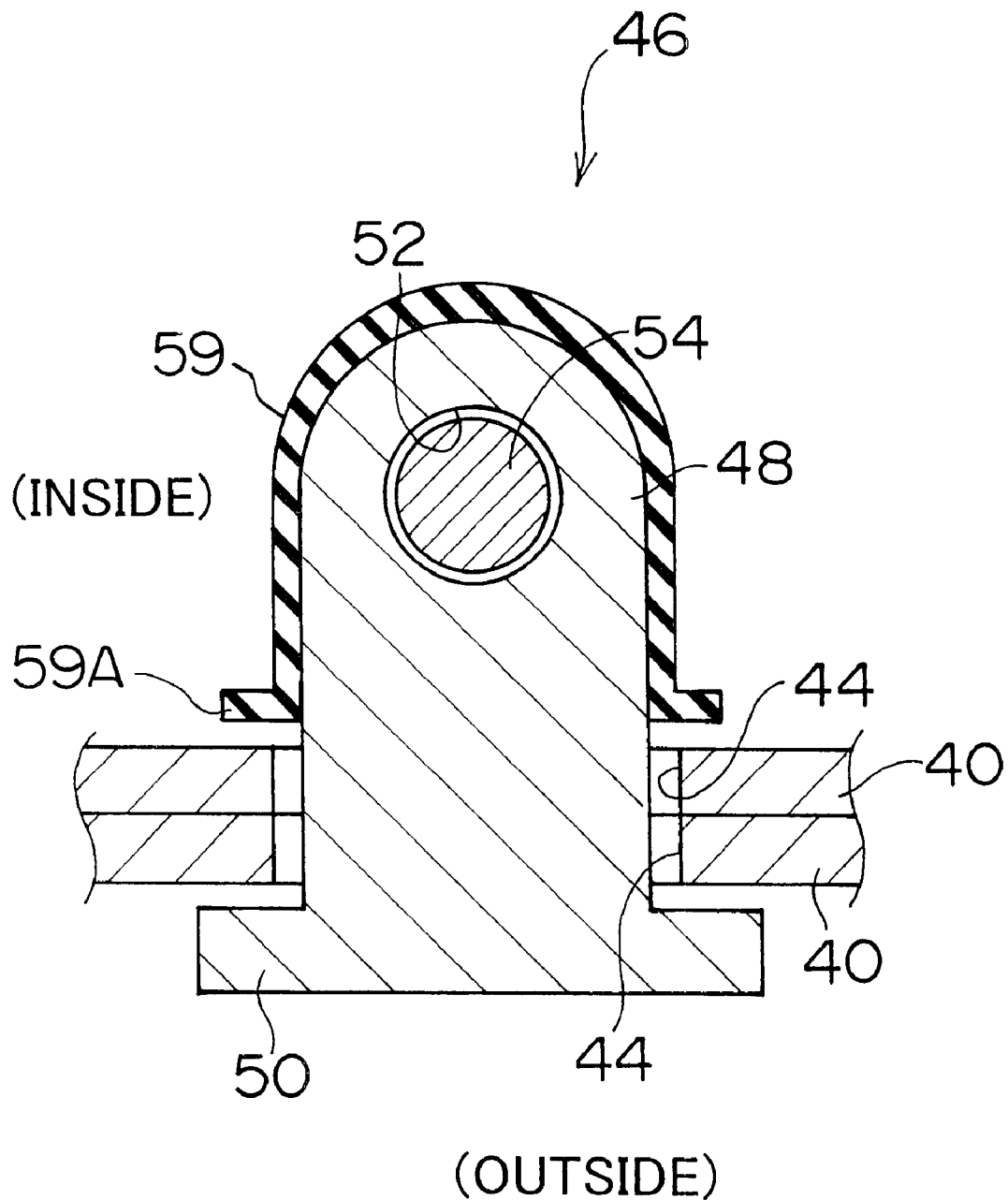

CURVED PART OF ENDOSCOPE

BACKGROUND OF THE INVENTION

1. Field of the Invention

The present invention relates generally to an endoscope, particularly to a curved part provided to an insertion part of an endoscope.

2. Description of Related Art

A base end of an insertion part of an endoscope is connected with a manual control part. A curved part is formed at the other end of the insertion part. The curved part is constructed by connecting a plurality of joint rings in the axial direction of the insertion part. Each joint ring comprises an annular main body and a connecting part, which is projected from the end of the main body. The main bodies of the joint rings are connected with each other at regular intervals by connecting the adjacent connecting parts of the joint rings. Curve control wires are inserted to the inside of the joint rings for controlling the curved part. On the inner periphery of the joint rings, a plurality of pins (guide members) are projected, and the curve control wires are inserted into guide holes formed at the ends of the pins.

Japanese Patent No. 2843370 discloses a curved part of an endoscope in which the pins are rotatably inserted in the inner periphery of the joint rings, and stoppers are formed at base ends, which are positioned at the outside of the joint rings, of the pins. The pins are prevented from falling into the inside of the joint rings by contact of the stoppers to the outer periphery of the joint rings; moreover the pins are also prevented from falling to the outside of the joint rings by inserting the curve control wires into the guide holes of the ends of the pins. With this construction, however, when the insertion part of the endoscope is assembled, the pins must be held from the outside during inserting the curve control wires into the guide holes of the pins in order to prevent the pins from falling to the outside of the joint rings; thus attaching the curve control wires causes some difficulties.

Many internal members, such as a light guide and a forceps tube, are arranged inside the insertion part of the endoscope. Then, as the curved part is controlled, the internal members touch with the projected part, such as the pins, and the internal members are damaged due to the large stress applied to them. The light guide, especially, is made of a bundle of glass fibers, and thus it is easily broken. In consideration of the problem mentioned above, Japanese Patent Application Laid-open No. 9-294710 discloses an endoscope in which the internal members are protected by covering them with resin tubes, cylindrical coil bodies, net tubes, and the like. However with this construction, an outer diameter of the curved part is made large because of the covering members, thus a filling rate of the curved part becomes adversely high. As the filling rate of the curved part becomes high, the internal members cannot smoothly move within the curved part because the internal members and the joint rings, or the internal members themselves interfere with each other, and the control of the curved part is adversely affected. Hence, the conventional endoscope needs a thicker curved part in order to reduce the filling rate.

The curved part is provided with a spare amount of angle so that the curved part can be curved by larger angles than it is required. For example, the curved part that requires 180 degrees of curving angle is constructed to be able to curve by approximately 210 degrees provided approximately 30 degrees of spare amount. However, with the construction of the conventional curved part of the endoscope, as the curved part is controlled, the curved part curves from the base end side, and the spare amount concentrates on the tip component side of the curved part; hence the tip component side cannot curve sufficiently. Then, a substantial length of the tip component, which is formed at the tip of the insertion part of the endoscope, becomes long and because of that the tip component cannot make small turns. A view area from a viewing window provided to the tip component is small and narrow as a result.

SUMMARY OF THE INVENTION

In view of the above-described circumstances, the present invention has as its object the provision of a curved part of an endoscope with curve control wires that can be inserted easily through guide holes of guide members.

Another object of the present invention is to provide a curved part of an endoscope that does not damage internal members of an insertion part of the endoscope, while an outer diameter of the insertion part can be narrowed.

Still another object of the present invention is to provide a curved part of an endoscope that can make a viewing area from a viewing window larger by sufficiently curving a tip component side of the curved part.

In order to achieve the above-described object, the present invention is directed to a curved part of an insertion part of an endoscope, comprising: a plurality of joint rings which are connected with each other along an axial direction of the insertion part; a plurality of guide members, each of the plurality of guide members being rotatably attached to an inner periphery of each of the plurality of joint rings, each of the plurality of guide members having a guide hole, each of the plurality of guide members having, on an outer periphery thereof, a first stopper preventing the guide member from falling into an inside of the joint ring and a second stopper preventing the guide member from falling to an outside of the joint ring; and a curve control wire which curves the curved part, the curve control wire being inserted in the guide holes of the plurality of guide members.

Accordingly to the present invention, the first and second stoppers are formed on the outer periphery of the body of the guide member; thus the guide member does not fall to either the inside or the outside of joint rings. Thus, the guide member does not have to be held when the curve control wire is inserted into the guide hole of the guide member, so that the curve control wire can be easily attached.

Preferably, a protection member is attached to the guide member or a projection formed at the inner periphery of the joint ring so as to protect an internal member provided in the curved part of the endoscope.

According to the present invention, since the protection member is attached to the projection, the internal member is not damaged even if the internal member touches the projection. Further, a filling rate of the insertion part of the endoscope is not large like in the case in which the internal member is covered with a protection member; thus, the insertion part of the endoscope can be narrowed.

In order to achieve the above-described object, the present invention is directed to a curved part of an insertion part of an endoscope, comprising: a plurality of joint rings which are connected with each other along an axial direction of the insertion part such that intervals between bodies of the adjacent joint rings become larger toward an tip component side of the curved part than a base end side of the curved part.

According to the present invention, the intervals between the bodies of the adjacent joint rings are larger at the tip component side than the base end side of the curved part; thus the tip component side is more easily curved than the base end side. Thereby, as controlling the curved part of the present invention, both the base end side and the tip component side are sufficiently curved so that the substantial length of the tip component is short. Thus, the tip component can make small turns, and hence a viewing area of a viewing window provided to the tip component is large.

BRIEF DESCRIPTION OF THE DRAWINGS

The nature of this invention, as well as other objects and advantages thereof, will be explained in the following with reference to the accompanying drawings, in which like reference characters designate the same or similar parts throughout the figures and wherein:

FIG. 4 is a longitudinal section view of a connecting pin in FIG. 2;

FIG. 7 is an explanatory view for the connecting pin in a shape different from the one in FIG. 4;

FIG. 9 is an explanatory view for the connecting pin in a shape different from the one in FIG. 4;

DETAILED DESCRIPTION OF THE PREFERRED EMBODIMENT

The preferred embodiments of a curved part of an endoscope of the present invention will be described in detail according to the accompanying drawings.

Figure 1:
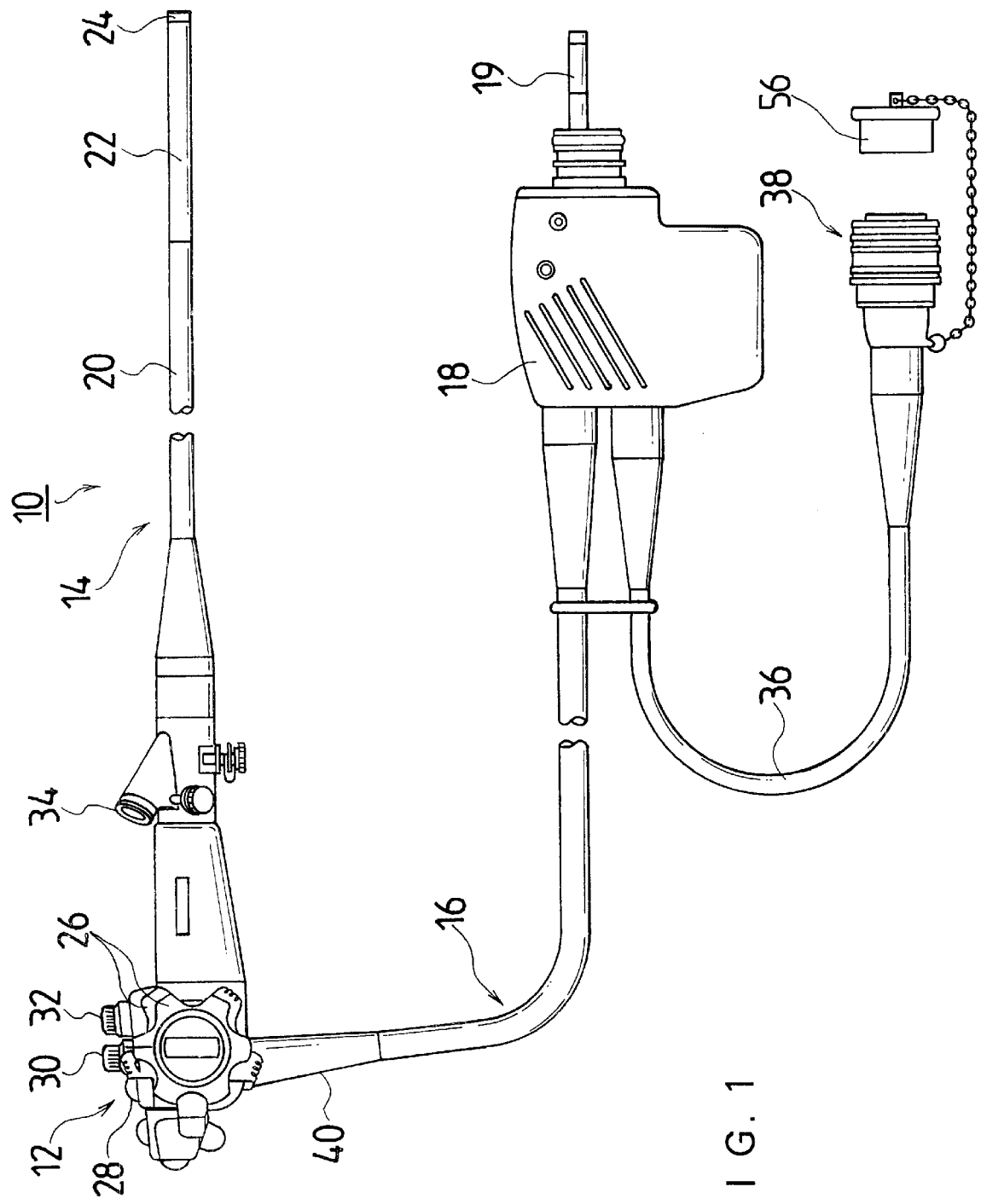
FIG. 1 is a view showing the entire structure of an endoscope to which a curved part of the present invention is applied.

As shown in FIG. 1, an endoscope 10, to which a curved part in the first embodiment of the present invention is applied, has a manual control part 12 and an insertion part 14 connected with the manual control part 12. The insertion part 14 is constructed of a soft part 20, a curved part 22, and a tip component 24. The curved part 22 is remotely controlled by rotating a pair of knobs 26 for curve control, which are provided to the manual control part 12, so that the tip component 24 is pointed to a desired direction.

The manual control part 12 is provided with a forceps aperture 34 for inserting operative tools such as forceps, and also provided with a shutter button 28, a suction button 30, an air and water supply button 32, and so forth. A light guide (LG) connector 18 is connected with the manual control part 12 via a universal cord 16. The LG connector 18 is provided with a light guide bar 19, which is connected with a light source device (not shown), and an electric connector 38 is connected with the LG connector 18 via an elastic tube 36. A cap 56 is provided to cover the electric connector 38.

Figure 2:
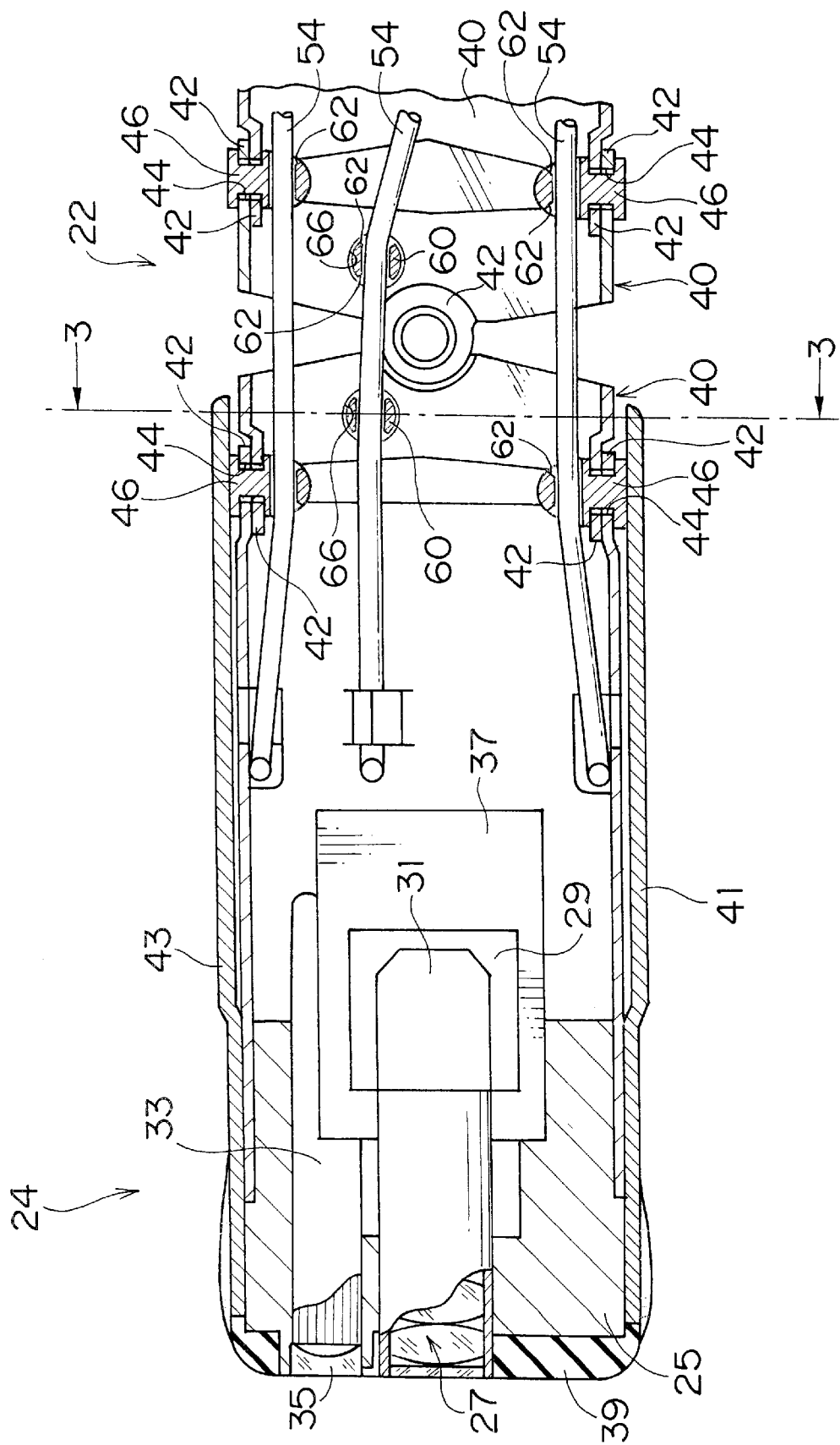
FIG. 2 is a longitudinal section view of the curved part in the first embodiment of the present invention.

As shown in FIG. 2, an objective optical system 27, which comprises a plurality of lenses, is provided inside of a body 25 of the tip component 24. The rear part of the objective lens system 27 is provided with a prism 31, and a solid-state imaging device (e.g., a CCD) 29 is provided to the exit side of the prism 31. A viewed image, which is taken-in by the objective optical system 27, is formed on a light-receiving face of the CCD 29 via the prism 31. The viewed image is converted into electric signals by the CCD 29, and the electric signals are outputted via a signal cable 45 (refer to FIG. 3) connected with a circuit board 37 to a processor (not shown) through the electric connector 38 in FIG. 1. The electric signals outputted to the processor are converted into video signals by a signal processing circuit and then outputted to a monitor (not shown). A light guide 33 in FIG. 2 is connected with the light guide bar 19 in FIG. 1; as the light guide bar 19 is connected with the light source device, illumination light from the light source device is projected from an exit end 33A of the light guide 33 via an illumination lens 35, which is provided to the tip component 24.

A cap 39, which is made of plastic, is attached to the end face of the body 25 of the tip component 24. An end joint ring 41 of the curved part 22 is connected at the base end side of the body 25, and an outer skin tube 43 covers the end joint ring 41 and the body 25.

The curved part 22 in FIG. 2 is constructed by connecting a plurality of joint rings 40 in the axial direction thereof. Four wires 54 (one of them not shown) for curve control are provided at regular intervals along the inner peripheral face of the joint rings 40. Respective ends of the curve control wires 54 are fixed to the end joint ring 41, which is connected with the tip component 24, and respective rear parts of the curve control wires 54 are connected and tensioned with pulleys (not shown), which are rotated by the curve control knobs 26 in FIG. 1. Thereby, when rotating the pulleys by operating the curve control knobs 26, the curve control wires 54 are pushed or pulled so that the curved part 22 is controlled in a desired direction.

A pair of overlaps 42, which are formed like tongues, are projected from each of the ends of the joint rings 40 in the axial direction. The pair of overlaps 42 are provided at every interval in 180 degrees, and formed at positions displaced by 90 degrees with respect to the overlaps 42 that are provided at the opposite end of the joint ring 40. Holes 44 are formed at respective overlaps 42. The overlaps 42 are overlapped with each other so that the overlaps 42 of the adjacent joint rings 40 and the holes 44 correspond with each other, and connecting pins (guide members) 46 are inserted into the holes 44 so that the joint rings 40 are rotatably connected.

Figure 3:
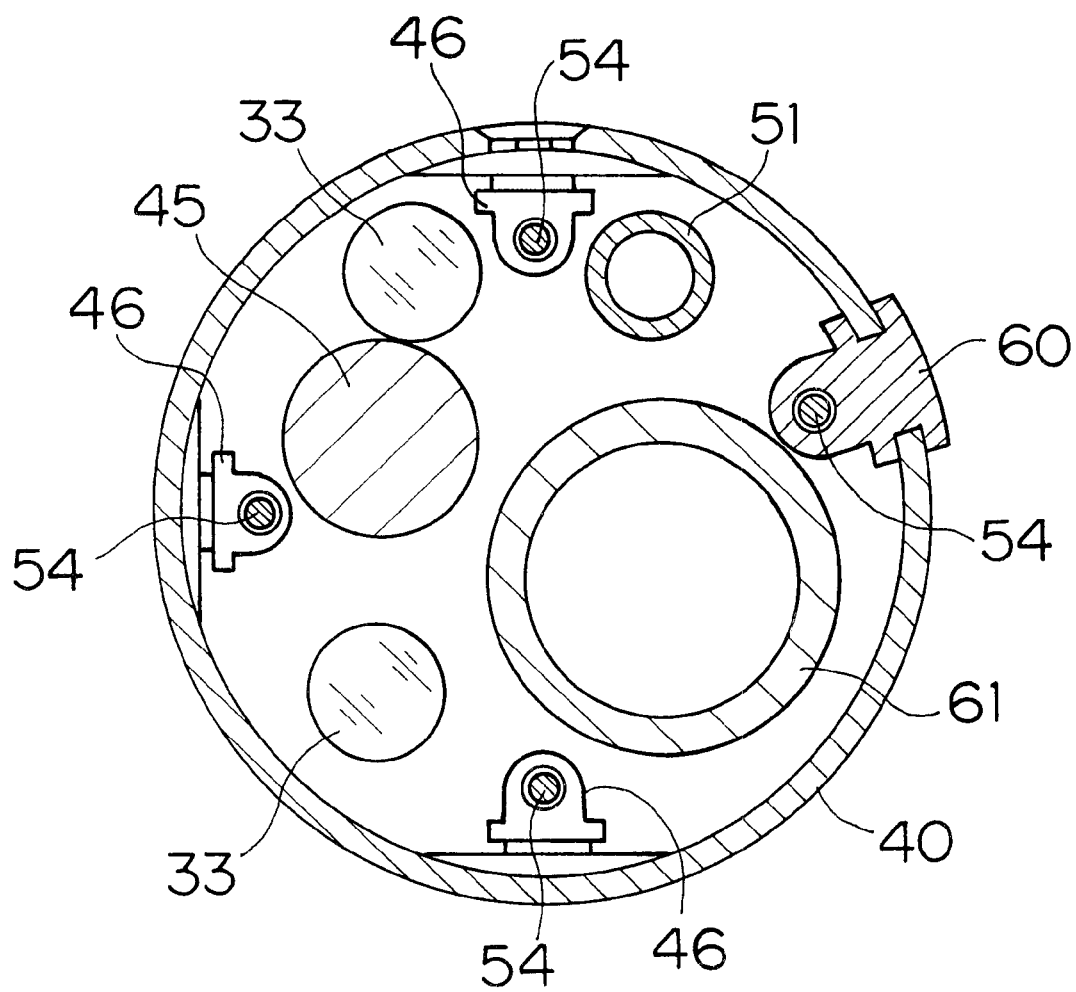
FIG. 3 is a section view of the curved part along line 3—3 in FIG. 2.

As shown in FIG. 3, the light guide 33, the signal cable 45, an air and water supply tube 51 and a forceps tube 61 are arranged inside the curved part 22.

As shown in FIG. 4, the connecting pin 46 is constructed mainly with a body 48 and an annular plate (second stopper) 58. The connecting pin body 48 is a cylinder having a slightly smaller diameter than the holes 44 of the overlaps 42. A flange (first stopper) 50 is formed integrally at an outer periphery of the base end of the connecting pin body 48. The flange 50 is formed to be larger than the holes 44 of the overlaps 42. Thus, as the connecting pin 46 is inserted into the holes 44 from the outside of the joint rings 40, the flange 50 contacts with the outer periphery of the joint ring 40, whereby the connecting pin 46 does not fall into the inside of the joint rings 40. A guide hole 52 is formed at the end of the connecting pin body 48 in a direction perpendicular to the axial direction of the body 48, and the curve control wire 54 is inserted in the guide hole 52. As shown in FIG. 2, the ends 62 of the guide holes 52 are chamfered in order to reduce friction between the curve control wires 54 and the guide holes 52.

An annular plate 58, which is formed with an elastic body such as rubber, is attached to the outer peripheral face of the connecting pin body 48. The annular plate 58 elastically deforms when the connecting pin body 48 is inserted into the holes 44, and, and then the annular plate 58 returns to its original shape after it passes through the holes 44. Thereby, the connecting pin 46 is rotatably attached to the joint rings 40 while it is being prevented from falling to the outside of the joint rings 40.

At the right side of the inside of the joint ring 40 in FIG. 3, since the forceps tube 61 is provided to and there is no space for attaching the connecting pin, a connecting pin 60 is attached to an unused space at the upper right of the forceps tube 61, and the curve control wire 54 is guided by the connecting pin 60. The connecting pin 60 is constructed in the same manner as the connecting pin 46, and the flange 50 and the annular plate 58 are provided to the outer peripheral face of the connecting pin body 48. The connecting pin 60 is inserted in holes 66 in FIG. 2, which are formed at the joint rings 40.

Next, an explanation will be given of operation the curved part of the endoscope that is constructed as described above.

Figure 5:
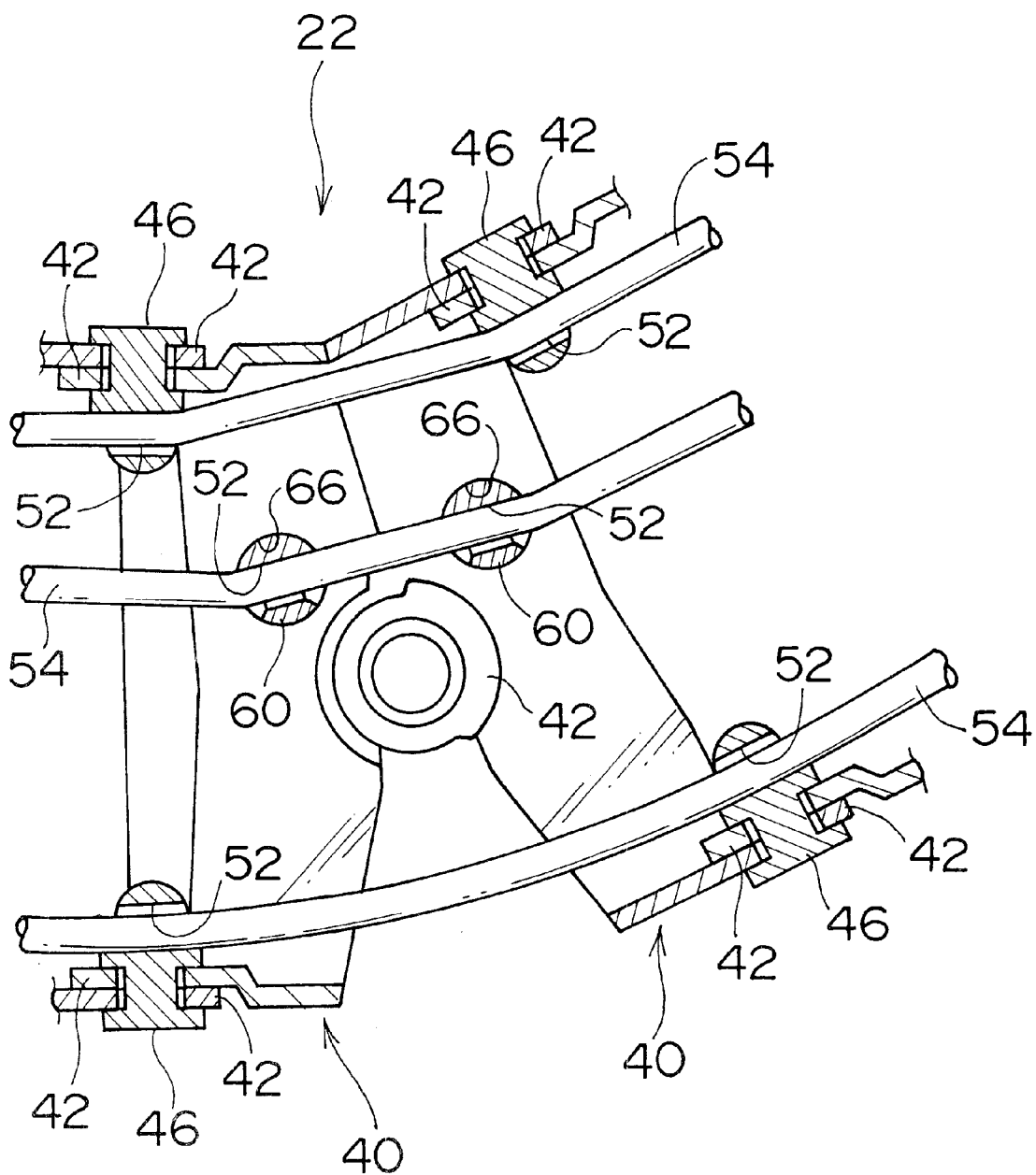
FIG. 5 is an explanatory view for the operation of the curved part in FIG. 2.

The curved part in this embodiment has the connecting pins 46 and 60, which are rotatably attached to the joint rings 40. Thus, when the curved part 22 is curved by pulling the curve control wires 54, the connecting pins 46 and 60 rotate by following the movement of the curve control wires 54. When the curved part 22 is curved as shown in FIG. 5 for example, the connecting pins 46 and 60 rotate so that the guide holes 52 are substantially parallel with the axis of the curved part 22. Thereby, friction force between the curve control wires 54 and the guide holes 52 is reduced when the curve control wires 54 are pulled, so that the curve control wires 54 can be smoothly pulled, and the curve control of the curved part 22 can be improved. Moreover, breaking of the curve control wire 54 can be prevented.

In the present embodiment, the flanges 50 and the annular plates 58 are provided to the outer peripheral face of the bodies 48 of the connecting pins 46 and 60, so that the connecting pins 46 and 60 fall neither the inside nor the outside of the joint rings 40. Thus, the connecting pins 46 and 60 do not have to be held from the outside of the joint rings 40 when the curve control wires 54 are inserted into the guide holes 52, and the curve control wires 54 can be easily attached.

As described above, in the present embodiment, since the flanges 50 and the annular plates 58 are provided to the outer periphery of the connecting pins 46 and 60 so as to prevent the connecting pins 46 and 60 from falling off the joint rings 40, the curve control wires 54 can be easily attached to the connecting pins 46 and 60.

Further in this embodiment, the curve control wires 54, which are guided by the connecting pins 46 and 60, never touch the joint rings 40 since the connecting pins 46 and 60 are restricted by the annular plates 58 to move to the outside of the joint rings 40; thus the curve control wires 54 can be smoothly pulled, and the control of the curved part 22 is improved.

Figure 6:
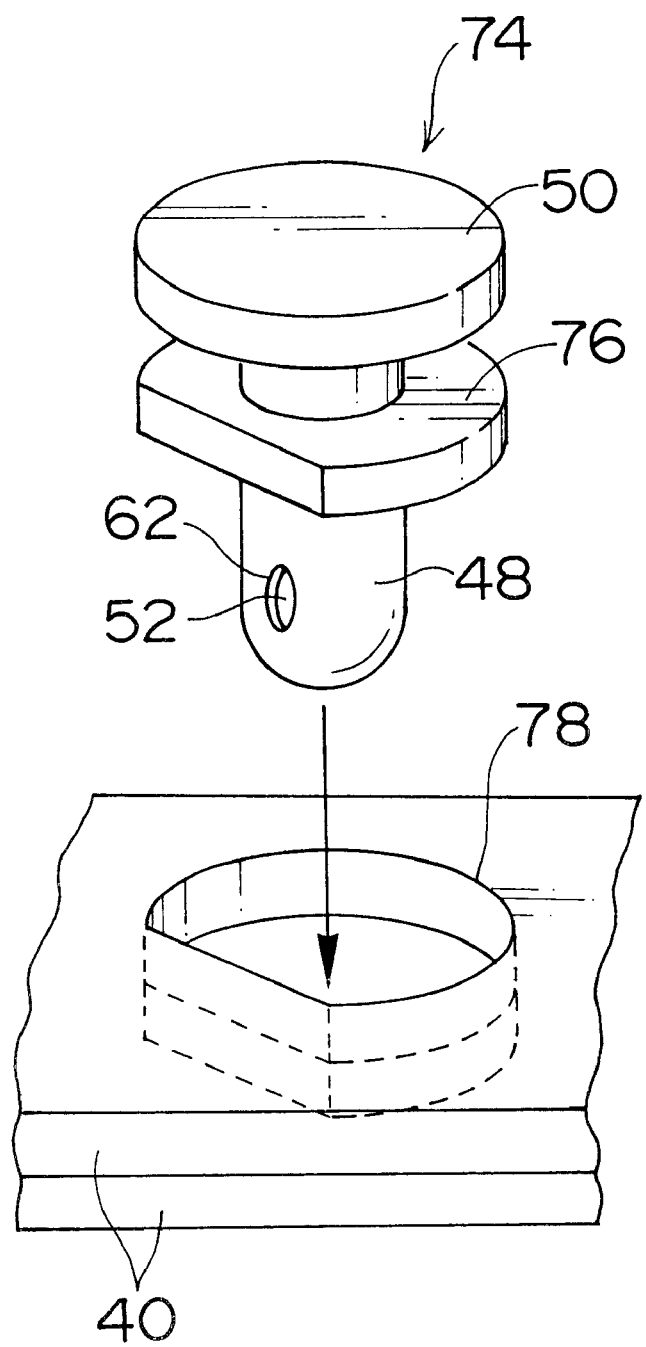
FIG. 6 is an explanatory view for the connecting pin in a shape different from one in FIG. 4.

The connecting pins 46 and 60 are not restricted in the form mentioned in the above-described example. As can be seen from one in FIG. 6 for example, the annular plate 76 of the connecting pin 74 and the holes 78 of the joint rings 40 can be in a D-shape, which is not circular. The annular plate 76 and the holes 78 are fitted and the connecting pin 74 is inserted, then the connecting pin 74 is rotated; thereby the connecting pin 74 do not fall off the joint rings 40 since the pin 74 engages with the joint rings 40. In this case, the annular plate 76 is not necessarily an elastic body, so that the connecting pin body 48 and the annular plate 76 can be formed integrally with the same material.

Moreover, as shown in FIG. 7, the flange side and the end side of the connecting pins 46 and 60 can be formed separately, and a flange side member 80 and an end side member 82 are connected to each other via the holes 44 of the joint rings 40 with adhesive or screwing so as to make them integral.

Figure 8:
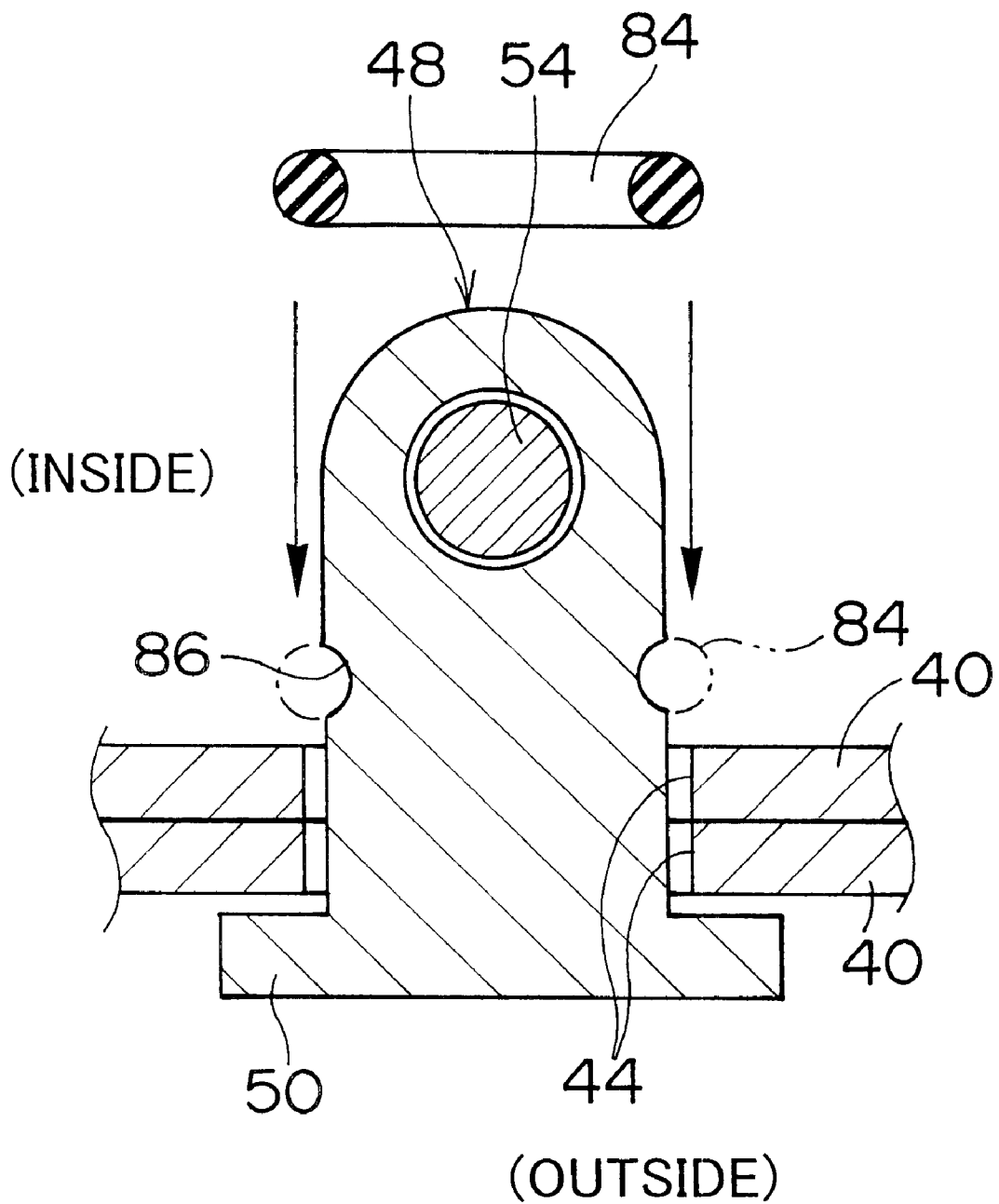
FIG. 8 is an explanatory view for the connecting pin in a shape different from the one in FIG. 4.

In the structure of the connecting pins 46 and 60, the annular plate 58 can be detachably attached to the connecting pin body 48. As can be seen from one in FIG. 8, a round groove 86 is formed at the outer peripheral face of the connecting pin body 48 using an O-ring 84 as the annular plate. The connecting pin body 48 is inserted into the holes 44 from the outside of the joint rings 40, and then the O-ring 84 is attached to the round groove 86 from the inside of the joint rings 40. Thereby, the O-ring 84 can be easily attached to or detached from the connecting pin body 48.

A cover member 59 in FIG. 9 is attached so as to cover the connecting pin body 48. The cover member 59 has a flange 59A, which corresponds to the annular plate 58 in FIG. 4 and prevents the connecting pin 46 from falling off the joint ring 40. The cover member 59 is formed with material that is softer (material with less hardness) than the outer peripheral face of the internal members (that are, the light guide 33, the signal cable 45, the air and water supply tube 51, and the forceps tube 61) of the curved part 22; thus the cover member 59 can serve as a protection member to prevent the internal members from being damaged by touching with the connecting pin body 48. The protection member will be described in detail in the second embodiment.

Figure 10:
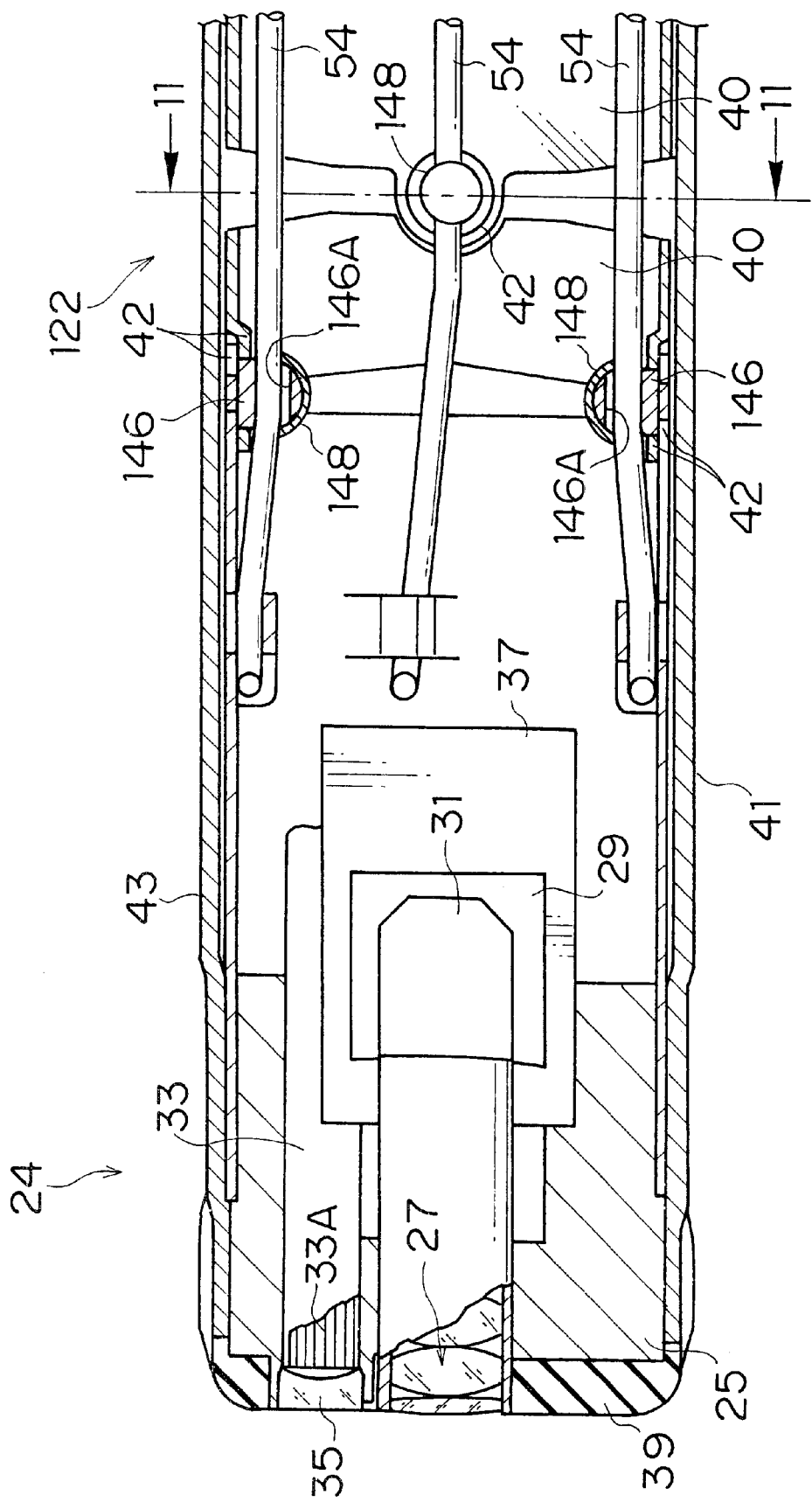
FIG. 10 is a longitudinal section view of the curved part in the second embodiment of the present invention.
Figure 11:
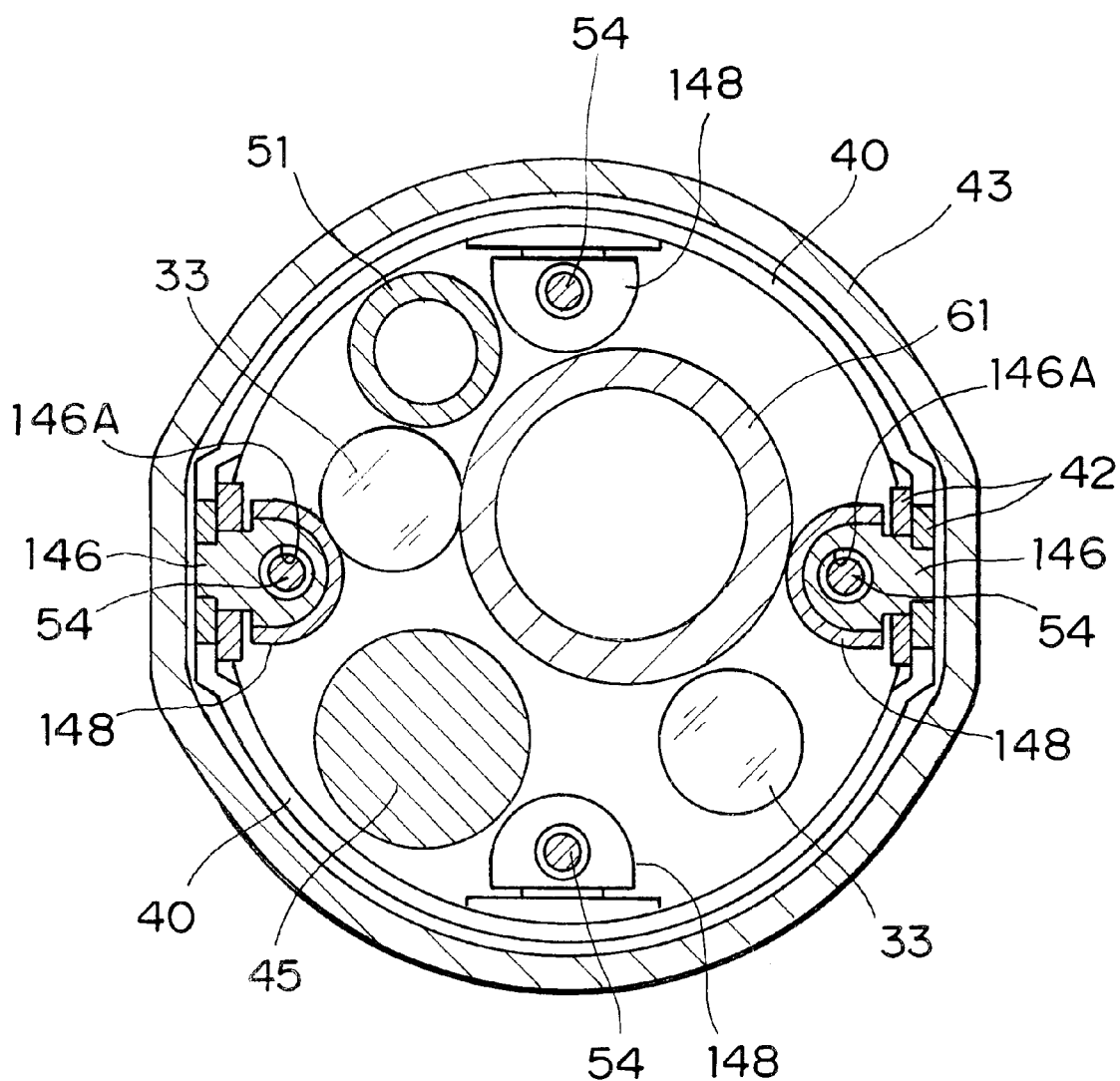
FIG. 11 is a section view of the curved part along line 11—11 in FIG. 10.

A curved part 122 of the endoscope for the second embodiment is shown in FIGS. 10 and 11. The same members as the first embodiment will be assigned the same reference numbers and the description for them will be omitted.

The curve control wire 54 is inserted into and guided by guide holes 146A of the connecting pins 146. The connecting pins 146 are projected from the inner peripheral face of the joint rings 40, and the guide holes 146A are formed at the projection parts.

Figure 12:
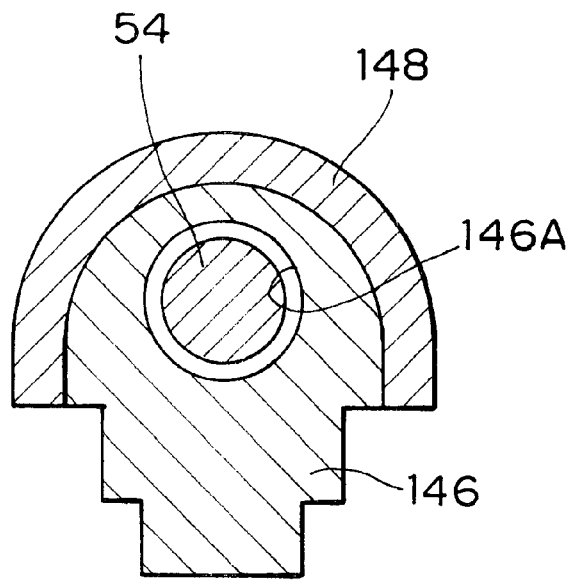
FIG. 12 is a section view of the connecting pin in FIG. 11.

As shown in FIGS. 11 and 12, a protecting member 148 is attached to the connecting pin 146. The protecting member 148 is in a form to cover the projection part of the connecting pin 146, and is attached to the end of the connecting pins 146 with adhesive. The protection member 148 is formed with material that is softer (material with less hardness) than the outer peripheral face of the internal members (that are, the light guide 33, the signal cable 45, the air and water supply tube 51, and the forceps tube 61) of the curved part 122. For example, if the light guide 33 and the signal cable 45 are covered by a silicone tube and the air and water supply tube 51 and the forceps tube 61 are covered by an urethane tube, the protection members 148 are made of rubber material such as silicone rubber, EPDM rubber, fluorine rubber, urethane rubber, and so forth.

Next, an explanation will be given of the operation of the curved part 122 of the endoscope in the second embodiment, which is constructed as presented above.

When controlling the curved part 122 by rotating the curve control knobs 26, which are provided to the manual control part 12 in FIG. 1, the internal members such as the light guide 33 and the signal cable 45 move within the curved part 122 and touch the connecting pins 146, which are projected from the inner peripheral face of the joint rings 40. However, since the protection members 148, made of rubber material, are attached to the connecting pins 146, the protection members 148 buff the touch, so that the internal members are not scratched or damaged. If the internal members are moved while being slid on the protection members 148 by pressure due to the controlling of the curved control 122, the internal members are not damaged even though scratches may occur to the protection members 148, because the protection members 148 are made of material softer than the internal members.

As described above, since the protection members 148 are attached to the ends of the connecting pins 146 of the curved part 122, damages caused by contact of the internal members with the connecting pins 146 when controlling the curved part 122 can be prevented.

In this embodiment, the protection members 148 are attached to the ends of the connecting pins 146, so that the filling rate of the curved part 122 is smaller than that in the case in which the outer peripheral face of the respective internal members is covered in its entirety. Therefore, the curved part 122, that is, the insertion parts 14, can be narrowed.

The material for the protection members 148 is not restricted to ones mentioned in the present embodiment; any material that can prevent scratches or damage of the internal members is allowable. For example, the protection member 148 is made of plastic such as polyfluoroethylene fiber, fluoro resin or silicone resin, or the like. In this case, the internal members smoothly slide when they contact with the protection members 148; thus resistance against the curve control of the curved part 122 is reduced and the curve control is satisfactory.

Figure 13:
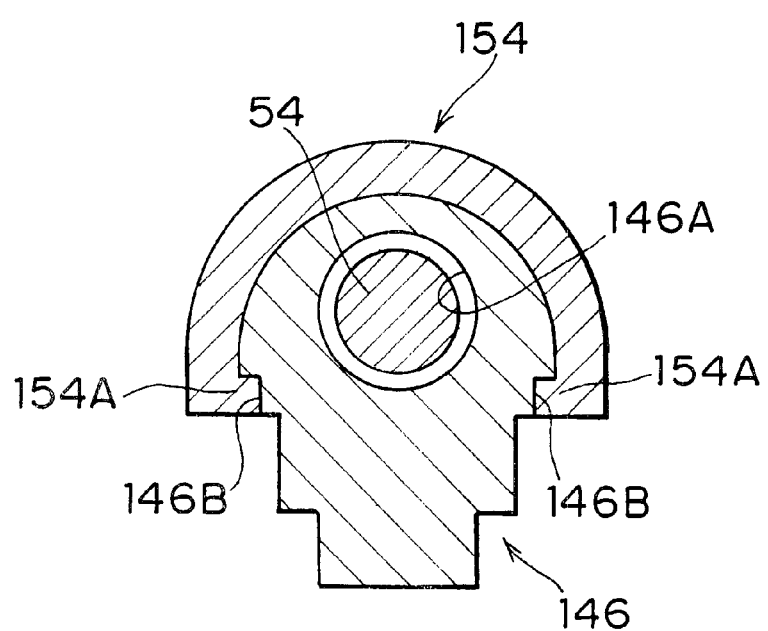
FIG. 13 is a section view of a protection member in a structure different from one in FIG. 12.

In the present embodiment, the protection member 148 is fixed to the connecting pin 146 with adhesive; however, the present invention does not limit such fixation. For example, a protection member 154 in FIG. 13 has an engage part 154A, which is projected and formed at the inside of the bottom end thereof, and the engage part 154A is engaged with a groove 146B, which is formed at the connecting pin 146. Thereby, the protection member 154 can be detachably attached to the connecting pin 146, and the protection member 154 can be easily exchanged when the protection member 154 is damaged or abraded.

Figure 14:
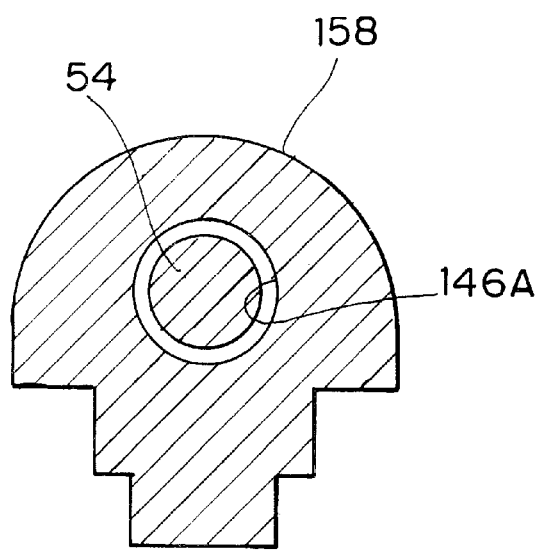
FIG. 14 is a section view of the protection member in a structure different from the one in FIG. 12.

A connecting pin 158 in FIG. 14 is an integral body in which the connecting pin 146 and the protection member 148 are formed integrally, and the material forming the connecting pin 158 is softer than the material for the internal members and is plastic, for example. Similar with the embodiment mentioned above, scratches or damage of the internal members can be prevented by this construction. Alternatively, the connecting pin 146 may be metal and coated with plastic and the like.

Figure 15:
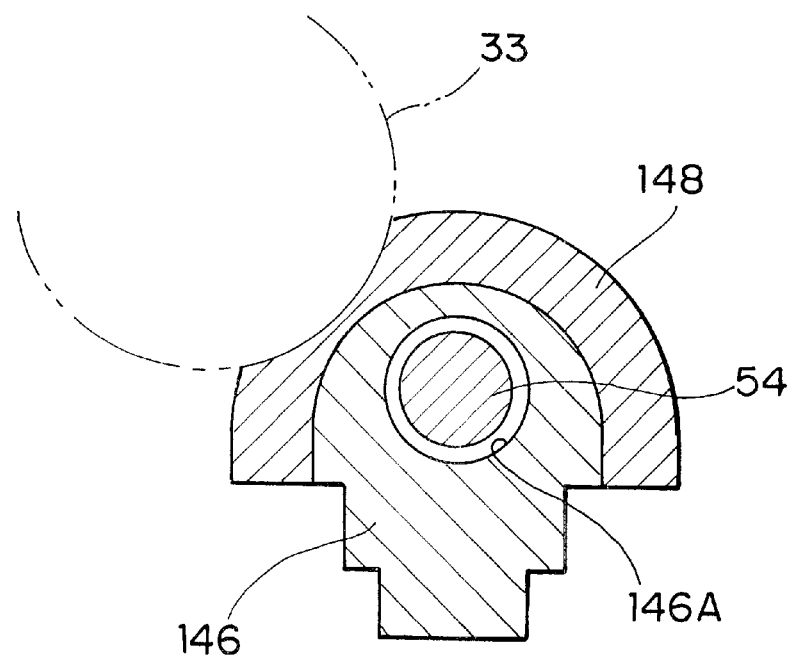
FIG. 15 is a section view of the protection member in a shape different from the one in FIG. 12.

The form of the protection member 148 is not restricted to the one in the present embodiment. For example, as shown in FIG. 15, a portion of the protection member 148 may be cut off in an arc shape. In this case, the protection member 148 and the internal member (e.g. the light guide 33) touch face to face, thus stress applied to the protection member 148 is reduced and the scratches or damage of the protection member 148 can be reduced. A form of the protection member 148 is not restricted to a form to cover the entire projection part from the joint rings 40 of the connecting pin 146; the protection member 148 may be attached to only a part with which the internal members touch. The protection members 148 may be attached to all the connecting pins 146, or attached to some of the connecting pins 146 that would come in contact with the internal members more often than other.

Figure 16:
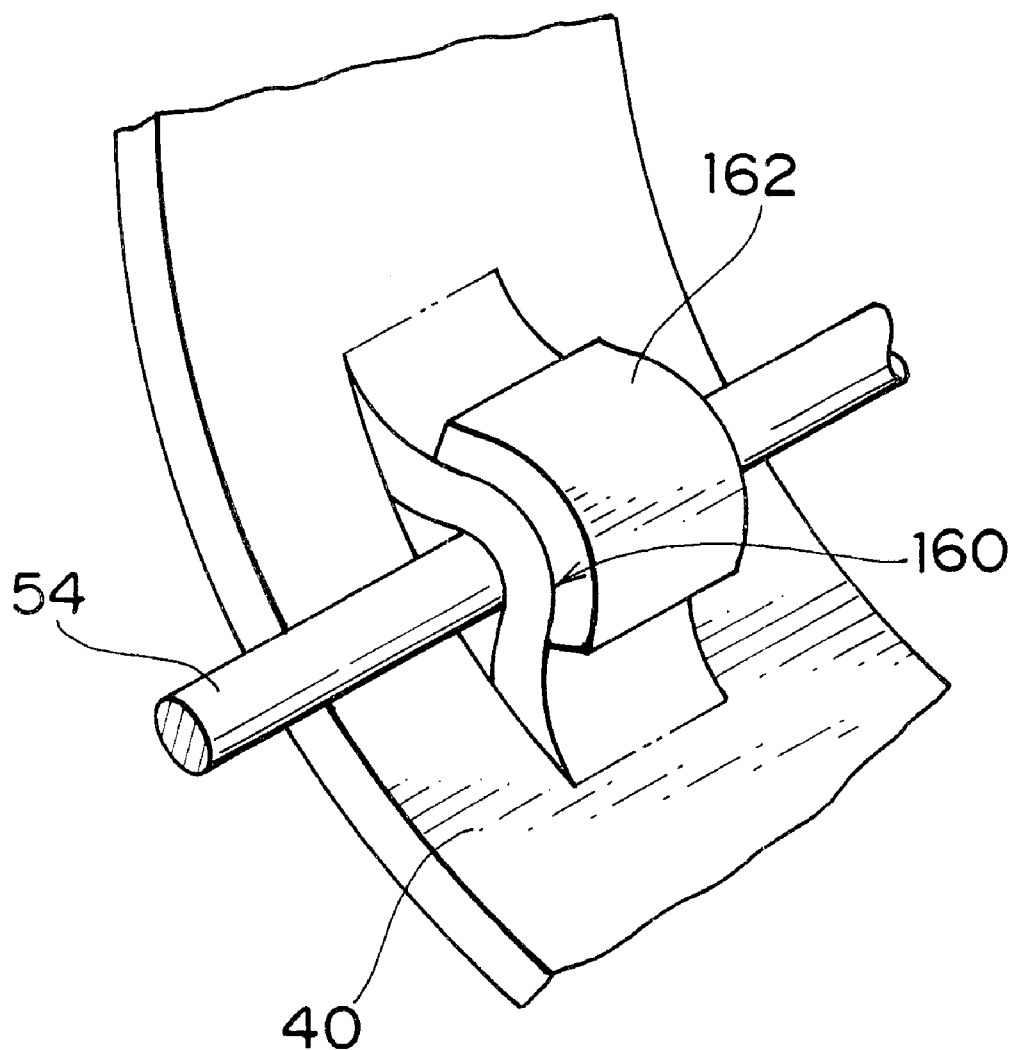
FIG. 16 is a perspective view of the protection member in a shape different from the one FIG. 12.

The projection parts to be covered with the protection members 148 are not restricted to the connecting pins 146. As can be seen from the one in FIG. 16, when a guide part 160 of the curve control wire 54 is formed by cutting and pressing the joint ring 40, the internal members are prevented from being damaged due to contact with the guide part 160 by attaching a protection member 162 to the top face of the guide part 160. In this case, the inside of the joint ring 40 may be coated with the protection member.

Further, the present invention is not restricted to the structure of the curved part 122; the present invention can also be applied to a soft tube of the endoscope, that are, the insertion part 14, the universal cord 16, and so forth.

Figure 17:
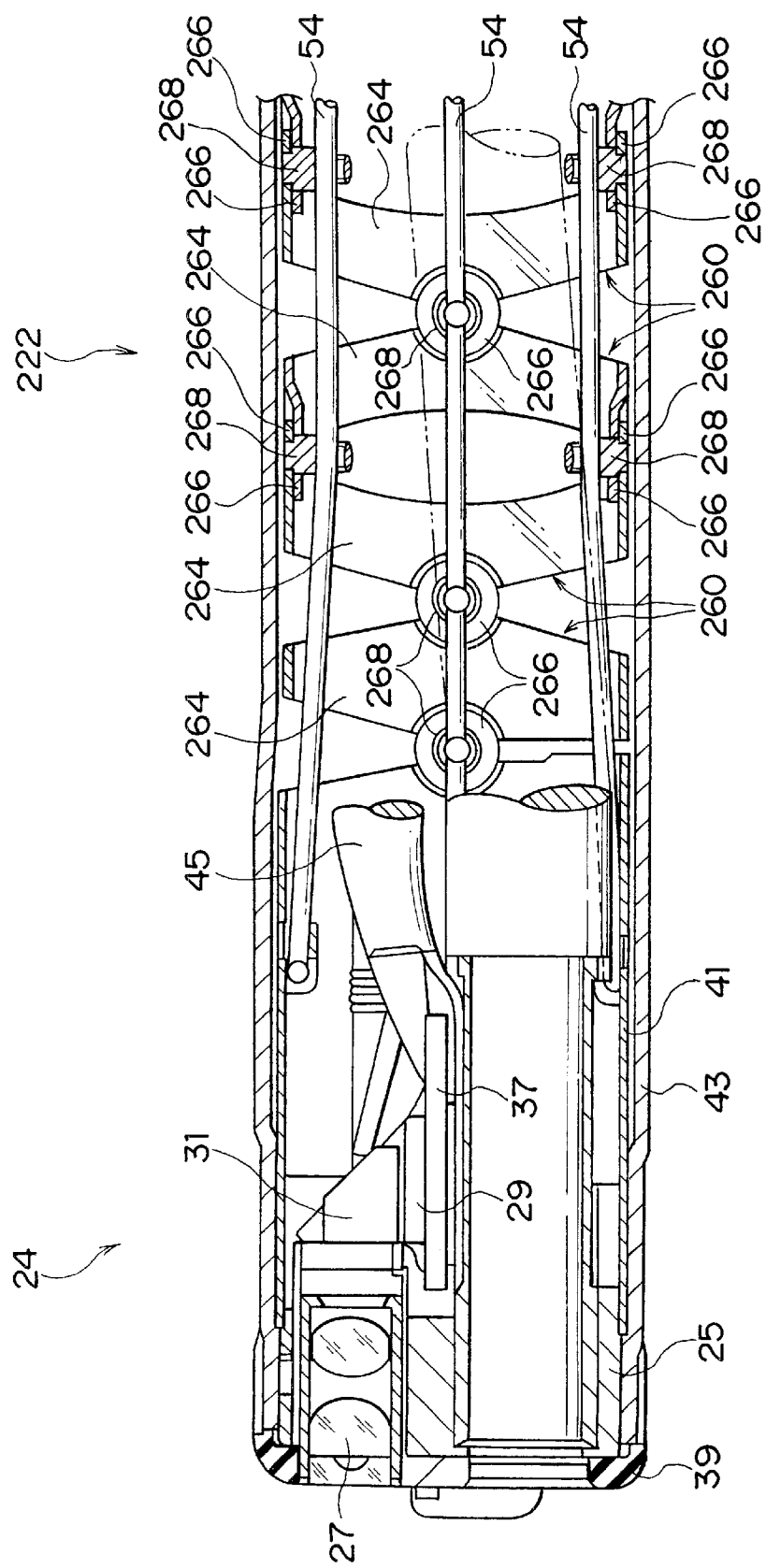
FIG. 17 is a longitudinal section view of the curved part in the third embodiment of the present invention.
Figure 18:
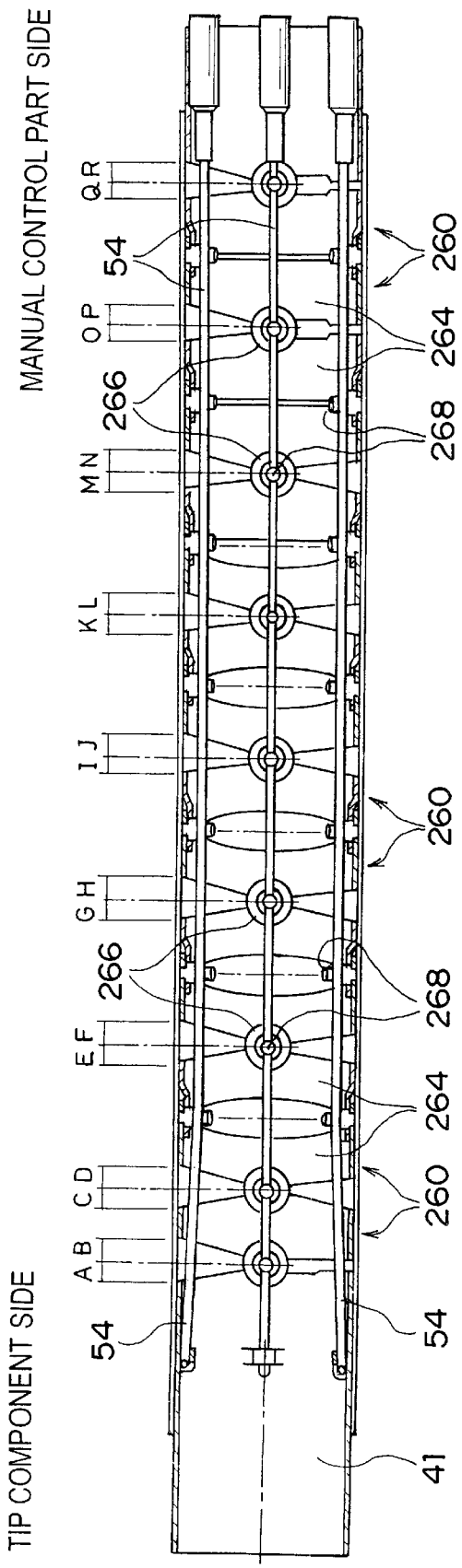
FIG. 18 is an explanatory view for the structure of the curved part in FIG. 17.
Figure 19:
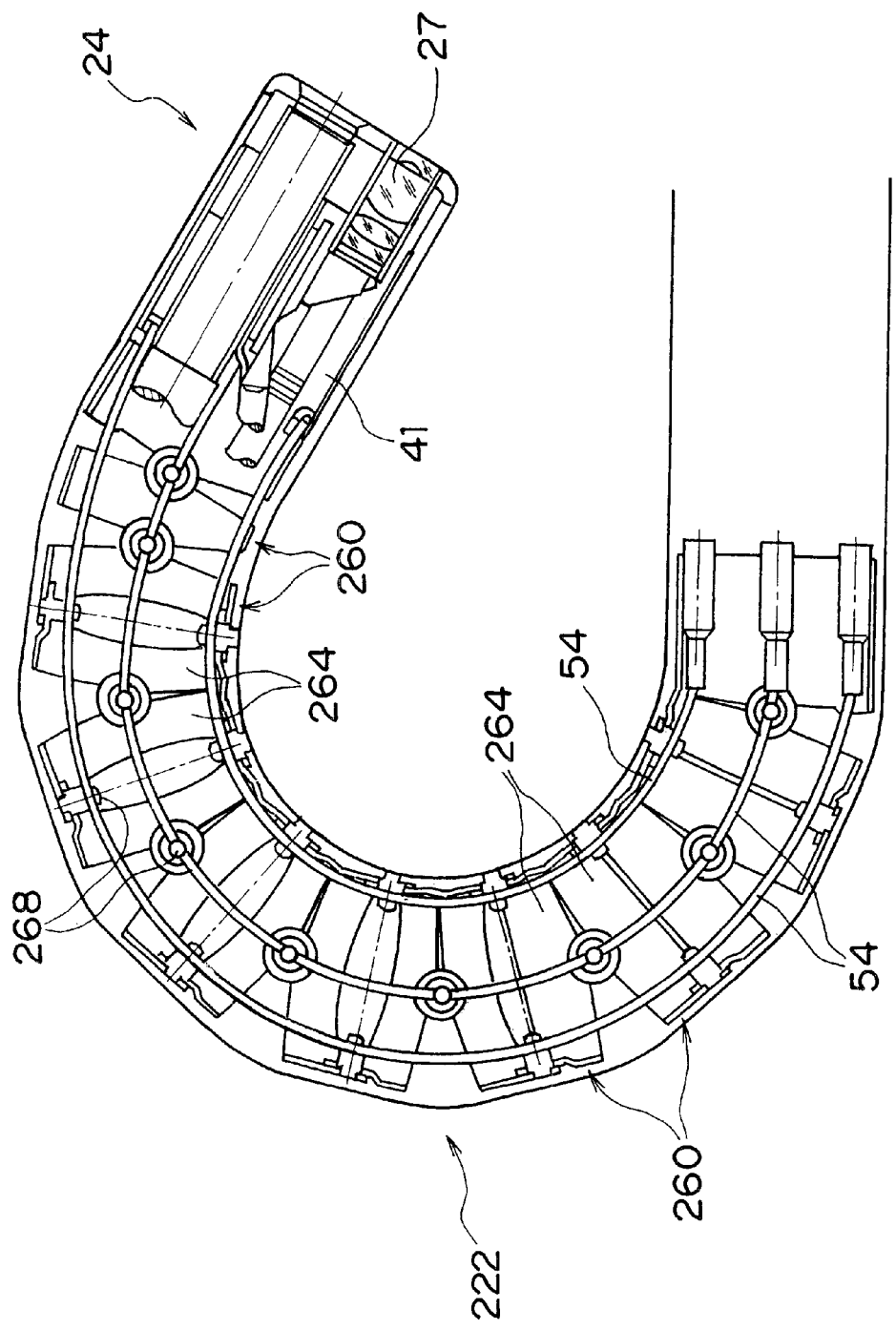
FIG. 19 is a view illustrating a state where the curved part in FIG. 18 is curved.

A curved part 222 of the endoscope in the third embodiment of the present invention is shown in FIGS. 17 and 18. The same members as the first embodiment will be assigned the same reference numbers and the description for them will be omitted.

The curved part 222 is constructed by connecting a plurality of joint rings 260 in the axial direction thereof. The joint ring 260 comprises a ring-shaped body 264 and connecting parts 266, which are projected at both ends of the joint ring body 264. The connecting parts 266 are provided with interval in every 180 degrees, and are overlapped with the connecting parts 266 of the adjacent joint ring 260. Then the connecting parts 266 of the adjacent joint rings 260 are connected by connecting pins 268 rotatably with each other.

As shown in FIG. 18, the joint ring body 264 has cut parts at their outer periphery that are apart from the connecting parts 266, and the joint ring bodies 264 of the adjacent joint rings 260 are connected with intervals. The intervals are formed so that they are gradually larger toward the tip component 24 side than the manual control part 12 side by altering the amount of cut of the joint ring bodies 264. Therefore, the width of intervals between the connected joint ring bodies 264 in FIG. 18 are: AB>CD>EF>GH>IJ>KL>MN>OP>QR. The joint rings 260 can rotate until the joint ring bodies 264 come in contact with each other. Thereby, the curved part 222 has a larger potential angle of curve at the tip component 24 side than the manual control part 12 side. Thus, the curved part 222 is made so that the curved part at the tip component 24 side is more easily curved than the manual control part 12 side. The curved part 222 has a spare amount of angle (e.g. 30 degrees), which is set so that the curved part 222 can be curved by a larger angle than it is required.

Next, an explanation will be given of the operation of the curved part 22 for the third embodiment, which is constructed as described above.

As rotating the curve control knobs 26, the curve control wires 54 are pushed or pulled and the curved part 222 is curved from the manual control part 12 side. At that point, since the curved part 222 is more easily curved at the tip component 24 side than the manual control part 12 side, the tip component 24 side of the curved part 222 can be curved sufficiently like the manual control part 12 side of the curved part 222 even though the spare amount is concentrated at the tip component 24 side. Thus, the entire curved part 222 is curved with substantially equal angles, that is, the curved part 222 is curved in an arc shape having substantially equal curvatures. As described above, the curved part 222 of the present embodiment is curved sufficiently with its entirety, so that the substantial length of the tip component 24 is shortened, and thus, the end of the insertion part 14 can make small turns. Thereby, the curve control in a small or narrow space is possible, and the viewing area from the objective optical system 27 of the tip component 24 can be larger.

The curved part 222 is curved in four directions that are up, down, right, and left, by pushing pulling the four curve control wires 54; however, in a case of the curved part that has a structure to be curved in a large angle in one direction, the intervals between the joint ring bodies 264 in only the one direction can be correspondingly set as presented above.

The intervals between the joint ring bodies 264 are allowable as long as they are larger toward the tip component 24 side than the manual control 12 side with respect to the entire curved part 222; for example, some of the intervals may be formed in a same size such as: AB=CD=EF>GH= IJ=KL>MN=OP=QR. Alternatively, only a part of the intervals at the tip component 24 side may be formed larger.

In the present embodiment, the intervals between the joint ring bodies 264 are adjusted by altering the amount of cut of the joint ring bodies 264; however the intervals may also be adjusted by altering lengths of the projections of the connecting parts 266, which are projected from the joint ring bodies 264.

Any curved part 222 is allowable as far as it is formed to have a larger angle at the tip component 24 side than the manual control part 12 side. For example, the connecting pins 268 are constructed for restricting the rotation angles between the joint rings 260 so that the rotation angle may be larger at the tip component 24 side than the manual control part 12 side.

Further, any curved part 222 is allowable as far as it is constructed to be curved more easily at the tip component 24 side than the manual control part 12 side. For example, contact faces of the connecting parts 266 are polished at the tip component 24 side so as to reduce the friction force between the connecting parts 266 and make them easier to curve at the tip component 24 side than the manual control part 12 side.

In the above-described embodiments, the examples are given with the electronic endoscope like the one in FIG. 1; however the present invention can also be applied to the endoscope for direct view with its manual control part 12 including an eyepiece.

As described above, according to the curved part of the endoscope of the present invention, the first stopper and the second stopper are provided to the outer peripheral face of the guide member body; thus the guide member does not have to be held as inserting the curve control wire into the guide hole of the guide member, whereby the curve control wire can be easily attached to the guide member.

Further, the protection member is attached to the projection on the inner peripheral face of the insertion part of the endoscope in order to prevent the internal members from being scratched or damaged; thus the filling rate of the insertion part of the endoscope is not large like the case where the internal members are covered with the protection members, and thus the insertion part of the endoscope can be narrowed.

Furthermore, the intervals between the bodies of the adjacent joint rings are larger at the tip component side of the curved part than the base end side of the curved part, so that the curved part is more easily curved at the end side. Thus, according to the curved part of the present invention, the tip component side of the curved part is sufficiently curved and the tip component can make small turns; therefore the viewing area can be larger.

It should be understood, however, that there is no intention to limit the invention to the specific forms disclosed, but on the contrary, the invention is to cover all modifications, alternate constructions and equivalents falling within the spirit and scope of the invention as expressed in the appended claims.

What is claimed is:

1. A curved part of an insertion part of an endoscope, comprising:

a plurality of joint rings which are connected with each other along an axial direction of the insertion part;

a plurality of guide members, each of the plurality of guide members being rotatably attached to an inner periphery of each of the plurality of joint rings, each of the plurality of guide members having a guide hole, each of the plurality of guide members having, on an outer periphery thereof, a first stopper preventing the guide member from falling into an inside of the joint ring and a second stopper preventing the guide member from falling to an outside of the joint ring; and a curve control wire which curves the curved part, the curve control wire being inserted in the guide holes of the plurality of guide members.

2. The curved part of the insertion part of the endoscope as defined in claim 1, wherein a protection member is attached to the guide member so as to protect an internal member provided in the curved part of the endoscope.

3. The curved part of the insertion part of the endoscope as defined in claim 2, wherein the protection member is made of material softer than the internal member.

4. The curved part of the insertion part of the endoscope as defined in claim 1, wherein a protection member is attached to a projection formed at the inner periphery of the joint ring so as to protect an internal member provided in the curved part of the endoscope.

5. The curved part of the insertion part of the endoscope as defined in claim 4, wherein the protection member is made of material softer than the internal member.

* * * * *